United States Patent [19]
Lolagne

[11] Patent Number: 5,618,305
[45] Date of Patent: Apr. 8, 1997

[54] FORCEPS WITH V-SHAPED GRASPING TIPS

[76] Inventor: Fritz Lolagne, 292 Ave. John Brown Bourdon, Port-au-Prince, Haiti

[21] Appl. No.: 375,423

[22] Filed: Jan. 18, 1995

Related U.S. Application Data

[63] Continuation-in-part of Ser. No. 252,209, Jun. 1, 1994, abandoned, which is a continuation-in-part of Ser. No. 94,627, Jul. 21, 1993, abandoned.

[51] Int. Cl.⁶ ............................................. A61B 17/00
[52] U.S. Cl. ................................ 606/205; 606/148
[58] Field of Search ........................... 606/139.8, 148, 606/205–210

[56]  References Cited

U.S. PATENT DOCUMENTS

| | | | |
|---|---|---|---|
| 3,828,791 | 8/1974 | Santos | 606/207 |
| 4,226,241 | 10/1980 | Walker, Jr. | 606/207 |

FOREIGN PATENT DOCUMENTS

| | | |
|---|---|---|
| 145976 | 3/1961 | U.S.S.R. . |
| 219095 | 5/1968 | U.S.S.R. . |
| 1321-409-A | 7/1987 | U.S.S.R. . |
| 2210574 | 6/1989 | United Kingdom . |

OTHER PUBLICATIONS

Brooks, Shirley M., Instrumentation for the Operating Room, Jun. 1981, p. 188.

*Primary Examiner*—Michael Powell Buiz
*Assistant Examiner*—Nancy Connolly Mulcare
*Attorney, Agent, or Firm*—Richard C. Litman

[57]  ABSTRACT

A forceps for grasping and manipulating tubular vessels of tissue, such as the vas deferens and the vagus nerve, comprises a needle-nose style grasping end with a clamping loop at the extreme tip. The hole has a beveled rear edge that aids in grasping an rotating tissue held in the loop. Arms of the forceps distal from the grasping end but ahead of a pivot point are serrated and interlock with one another when the forceps is closed. An alternate embodiment of the invention has the same novel tip, but has longer handles and is suitable for manipulation of the vagus nerve. Also provided is a method of using the forceps for performing a vasectomy.

5 Claims, 5 Drawing Sheets

FORCEPS WITH V-SHAPED GRASPING TIPS

CROSS REFERENCE TO RELATED APPLICATION

This application is a Continuation-in-Part of application Ser. No. 08/252,209, filed Jun. 1, 1994, now abandoned, which was a Continuation-in-Part of application Ser. No. 08/094,627, filed Jul. 21, 1993, now abandoned.

BACKGROUND OF THE INVENTION

1. Field of the Invention

The present invention relates generally to surgical implements for gripping tissue, and more particularly to forceps used in conducting vasectomies and surgical interventions in the lower esophagus or stomach.

2. Description of the Prior Art

Voluntary surgical contraception, also called contraceptive sterilization, has become the most widely used method of family planning in the world. It is also one of the safest and most economical contraceptive methods. The health benefits of contraceptive sterilization are especially evident in developing countries where temporary contraceptive methods may be periodically in short supply or used ineffectively, and where unwanted pregnancies carry a high risk of maternal death. Contraceptive sterilization may be performed on either the female (tubal ligation), or the male (vasectomy). Although both procedures are equally effective as contraceptive methods, vasectomy is simpler, safer, and less expensive than tubal ligation.

Vasectomies can be accomplished by cutting or clipping the vas deferens. Because of the relatively high failure rate of the clipping method, cutting is preferred. In the cutting method, a forceps is used during the vasectomy procedure to grasp and elevate the vas deferens, the duct which transports sperm and semen from the testicles to the penis. The vas deferens is elevated and exposed so that it may be cut and ligated, thus completely preventing the flow of sperm in the vasectomized male. In a standard vasectomy, the vas deferens is isolated, the grasping tips of forceps are clamped behind it, and the duct is elevated. Once having elevated the vas deferens, the surgeon rotates it, thus exposing its surrounding sheath, which is then dissected to uncover the duct.

A commonly used instrument in performing vasectomy is a standard forceps, such as Allis forceps. The standard forceps used in vasectomy comprises a scissors-like construction that includes a locking mechanism for the two arms at the handle end. The grasping tips, at the ends of the arms opposite the handles, have mating sawtooth extensions, which meet in a line perpendicular to the lengthwise extension of the instrument.

Because of the large area defined by the tips of standard forceps, additional tissue is often grasped and elevated along with the vas deferens. The large end structure defined by the standard forceps also frequently permits the vas deferens to escape the surgeon's grasp as he pulls it up and out of the incision. Finally, due to the large open area defined by the closed ends of the grasping tips and the pivot point of the two arms, the vas deferens often slips out of the grasp of the instrument when the duct is rotated to expose the surrounding sheath. In each case, the surgeon is required to recapture the duct, and recommence this part of the procedure. Such imprecision and slippage renders the procedure longer, and more difficult to conduct than if a forceps with a design more specific to the procedure were used.

Several attempts have been made to overcome the problems associated with the use of standard forceps in procedures requiring manipulation of ducts such as the vas deferens. U.S. Pat. No. 2,397,823, issued to Carl W. Walter, on Apr. 2, 1946, discloses a forceps intended to be capable of grasping a wide variety of objects. This forceps has a elongated "pistol-grip" handle. It is oriented at an angle of at least 45 degrees relative to a gripping portion of the device. Consequently, minute manipulations of tissue during a surgical procedure would be cumbersome at best, and dangerous at worst.

Moreover, the forceps is shown to have serrations on the very tip. Such serrations, while providing additional gripping friction, would necessarily cause destruction of surrounding tissue. Also, the presence of these serrations clearly indicate that this forceps has a clamping hole substantially recessed from the end of the device, in stark contrast with applicant's own invention. Use of such a device in a vasectomy procedure would:

require an extraordinarily large incision in the scrotum for insertion of the device, leading to increased likelihood of infection;

cause tissue damage while the device is passed into the scrotum sufficiently far for the clamping hole to engage the vas deferens;

cause tissue damage when the device is closed and clamped around the vas deferens, because tissue behind the vas deferens would necessarily be clamped in addition;

make the vasectomy procedure's lifting and turning of the vas deferens impossible without substantial destruction of surrounding tissue, because of additional tissue caught in the large extension of the forceps' tips beyond the clamping hole; and, result in additional, unwarranted procedure length, trauma, and danger.

This device also fails to have a beveled rim around the edge of the hole nearer its grasping end to provide effective gripping for rotation of a vas deferens or other tubular tissue. Instead, it has "arcs of different curvature" disposed around the rims of recesses in the jaws, which are described as including an "almost blade-like inner edge." Such bladed arcs would tend to cut tissue held, making holding of tissue impractical. In fact, the forceps is intended for use with objects other than tissue, such as needles and swabs. Importantly, the literature describing the use of this device does not even mention use for vasectomies.

U.S. Pat. No. 2,642,871, issued to Joseph Theurig, on Jun. 23, 1953, discloses a forceps suitable for grasping tubular objects, such as syringes. The forceps has a clamping aperture described and depicted as comprising "transverse inverted obtuse angular meeting faces." The difficulty concomitant of using such a device in a vasectomy procedure is substantial. Because the aperture is not curved to the shape of a tubular duct, the vas deferens would tend to slide around within the aperture, if the device were sufficiently large to allow full closure with the tips actually contacting one another. Such sliding would make performance of the procedure impossible because the appropriate cutting and knotting of the duct would be unfeasible. Making the device smaller, so that the device would immovably hold the vas deferens, would result in failure of the device to close completely, as shown in FIG. 4 of the Theurig patent. Without complete closure, the device would tend to allow undesired release of the vas deferens during the required lifting and twisting of the vas deferens.

The Theurig forceps also lacks a beveled rim around the edge of the hole nearer its grasping end to provide effective gripping for rotation of a vas deferens or other tubular tissue. Notably, the literature referring to the use of this device does not even mention use for vasectomies.

U.S. Pat. No. 5,067,958, issued to Jeffrey J. Sandhaus, on Nov. 26, 1991, demonstrates a complicated apparatus intended to be used in procedures for implanting locking clips for clamping and occluding tubular vessels, such as the vas deferens during a vasectomy. In addition to the ancillary concerns about cost, ease of construction and maintenance, this device has several practical shortcomings in regard to use and teaching in relation to vasectomy forceps and vasectomy procedures. One problem is that it relies on clamping of the vas deferens, rather than cutting it; consequently, the desired sterilization cannot be completely ensured by the use of this device. Another problem is that its complicated operation requires special training for use, and requires additional pre-surgical preparation time. A third problem is that while the device shows a curved clamping hole appropriate for immovably holding a tublar vessel with the tips contacting one another, the clamping hole is relatively far removed (in comparison with applicant's own invention) from the end of the apparatus, as shown in FIG. 45 of the Sandhaus patent. Use of such a device in a vasectomy procedure, even if for allowing cutting and ligating instead of clipping, would:

require an extraordinarily large incision in the scrotum for insertion of the device, leading to increased likelihood of infection;

cause tissue damage while the device is passed into the scrotum sufficiently far for the clamping hole to engage the vas deferens;

cause tissue damage when the device is closed and clamped around the vas deferens, because tissue behind the vas deferens would necessarily be clamped in addition;

make the vasectomy procedure's lifting and turning of the vas deferens impossible without substantial destruction of surrounding tissue, because of additional tissue caught in the large extension of the forceps' tips beyond the clamping hole; and, result in additional, unwarranted procedure length, trauma, and danger.

The Sandaus forceps also fails to provide a beveled rim around the edge of the hole nearer its grasping end to provide effective gripping for rotation of a vas deferens or other tubular tissue.

British Patent No. 2,227,200, issued to Malcolm Charles Holbrook, on Jul. 25, 1990, discloses a forceps used for holding a catheter or organ duct during the course of a surgical procedure. This forceps has a three-millimeter clamping hole centered five millimeters from the end of the forceps, a relatively large distance (many times as large as the applicant's own invention) that makes the device unusable for a vasectomy procedure. This forceps was designed for its invisibility to X-rays used during a surgical procedure, and not for use in vasectomies. Use of such a device in a vasectomy procedure, where X-rays are unnecessary, would:

require an extraordinarily large incision in the scrotum for insertion of the device, leading to increased likelihood of infection;

cause tissue damage while the device is passed into the scrotum sufficiently far for the clamping hole to engage the vas deferens;

cause tissue damage when the device is closed and clamped around the vas deferens, because tissue behind the vas deferens would necessarily be clamped in addition;

make the vasectomy procedure's lifting and turning of the vas deferens impossible without substantial destruction of surrounding tissue, because of additional tissue caught in the large extension of the forceps' tips beyond the clamping hole; and, result in additional, unwarranted procedure length, trauma, and danger.

The Holbrook forceps also lacks a beveled rim around the edge of the hole nearer its grasping end to provide effective gripping for rotation of a vas deferens or other tubular tissue.

The large end design of the Holbrook patent, with its clasping, rather than grasping function, explains why it is in fact not the instrument of choice in performing vasectomies. Instead, surgeons most commonly use the standard or Allis forceps, or the Sandhaus forceps, to perform this procedure. Although vasectomy can be performed with either of these latter two instruments, each presents definite disadvantages, described above, that are resolved by use of the present applicant's invention.

None of the above inventions and patents, taken either singly or in combination, is seen to describe the instant invention as claimed.

SUMMARY OF THE INVENTION

The forceps of the present invention anticipates and resolves the problems inherent in the prior art by means of a small end structure, comprising an oval-shaped, closed loop, defined by the closed ends of beveled grasping tips and a series of mating serrations immediately adjacent to the loop. This loop is approximately 0.40 centimeters in diameter in a direction parallel to arms of the forceps and 0.25 centimeters in diameter in a direction perendicular to arms of the forceps. The shape and size of this closed loop permits the surgeon to firmly grasp the vas deferens and surrounding sheath, to elevate it up and out of the incision, and to rotate it all in one movement, thus exposing the surrounding sheath in order to facilitate its dissection. Once the duct is thus exposed by the invention, it can be easily cut and ligated. The mating serrations, which form a line following the lengthwise extension of the instrument, provide a continuous, firmly closed line behind the loop. This innovation further reduces slippage of the vas deferens when it is rotated during the vasectomy procedure.

In a vasectomy as performed with the standard forceps design, the surgeon must create an excessively large scrotal incision, grasp the vas deferens, elevate it out of the incision, and rotate it to expose the outside sheath for dissection. In the process of such a vasectomy, additional tissue is grasped and damaged, and the vas deferens slips with such frequency that effective cutting and ligation of the vas deferens is difficult and time-consuming. In contrast, the minute, beveled, curved loop of the present invention allows for a smaller incision with more accurate grasping, reduces slippage during this part of the procedure, and assures that no tissue other than the vas deferens is grasped. In fact, the applicant has found in his own medical practice that the present forceps are easier, faster, safer and generally much preferable to use in the course of performing vasectomies, as compared to use of standard forceps.

Thus, the present invention provides numerous advantages over the standard forceps design used in conducting vasectomies, including but not limited to:

(1) Use of the invention reduces the risk of slippage of the vas deferens during vasectomy. The invention involves an oval-shaped grasping opening, which allows the vas deferens to be more easily and securely grasped and rotated than does the standard design.

(2) Because the risk of slippage during the procedure is diminished, the invention reduces the time needed to conduct the procedure. A vasectomy can be accomplished using the invention in approximately six to eight minutes, as compared with more than fifteen to twenty minutes using the standard forceps design. This reduction is achieved without changing the technique used for the procedure. Since most vasectomies are performed using local anesthesia, a reduction in the time necessary to conduct the procedure means the operation can be accomplished more safely and with less discomfort to the patient.

(3) The smaller end structure of the present invention allows for a smaller incision to be made than that necessary with the standard forceps. A smaller incision leads to reduced risk of infection following the procedure, and provides an added cosmetic benefit to the patient.

All of the described advantages of the invention forceps in grasping, pulling and elevating the vas deferens during vasectomy may be equally applied to an alternate embodiment of the invention, useful for surgical interventions in the stomach or lower esophagus, wherein the vagus nerve is grasped and elevated. However, the vagus nerve usually is not rotated as is the vas deferens during a vasectomy. In this alternate embodiment of the invention, the arms of the forceps are approximately six centimeters longer, thereby providing additional reach necessary in surgical interventions in the lower esophagus and stomach.

Accordingly, it is a principal object of the invention to reduce the risk of slippage of the vas deferens during vasectomy by providing an oval-shaped grasping aperture, which allows a user to grasp and rotate the vas deferens more easily and securely than does the standard design.

It is another object of the invention to reduce the time needed to conduct a vasectomy procedure, preferably to between six and eight minutes, by reducing the risk of slippage during the procedure, as compared to using the standard forceps design, without changing the technique used for the procedure.

It is a further object of the invention to reduce discomfort and increase the safety of patients undergoing vasectomies under local anesthesia by reducing the time necessary to conduct the vasectomy procedure.

Still another object of the invention is to allow for a smaller incision to be made during a vasectomy procedure than that necessary with standard forceps by providing a smaller end structure, thereby leading to reduced risk of infection following the procedure and producing less cosmetic damage.

An additional object of the invention is to provide a forceps suited for excellent characteristics for use in vasectomies that can alternately be used in operations involving the vagus nerve, merely by adding length to the forceps handle.

A still further object of the invention to provide a forceps having a grasping opening, as opposed to a clamping opening, of a size and shape which prevents slippage of the vas deferens during the performance of a vasectomy, or of the vagus nerve during interventions in the lower esophagus or stomach.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention can be more fully appreciated with reference to the accompanying Figures, in which like numerals refer to like portions thereof.

Figure 2:
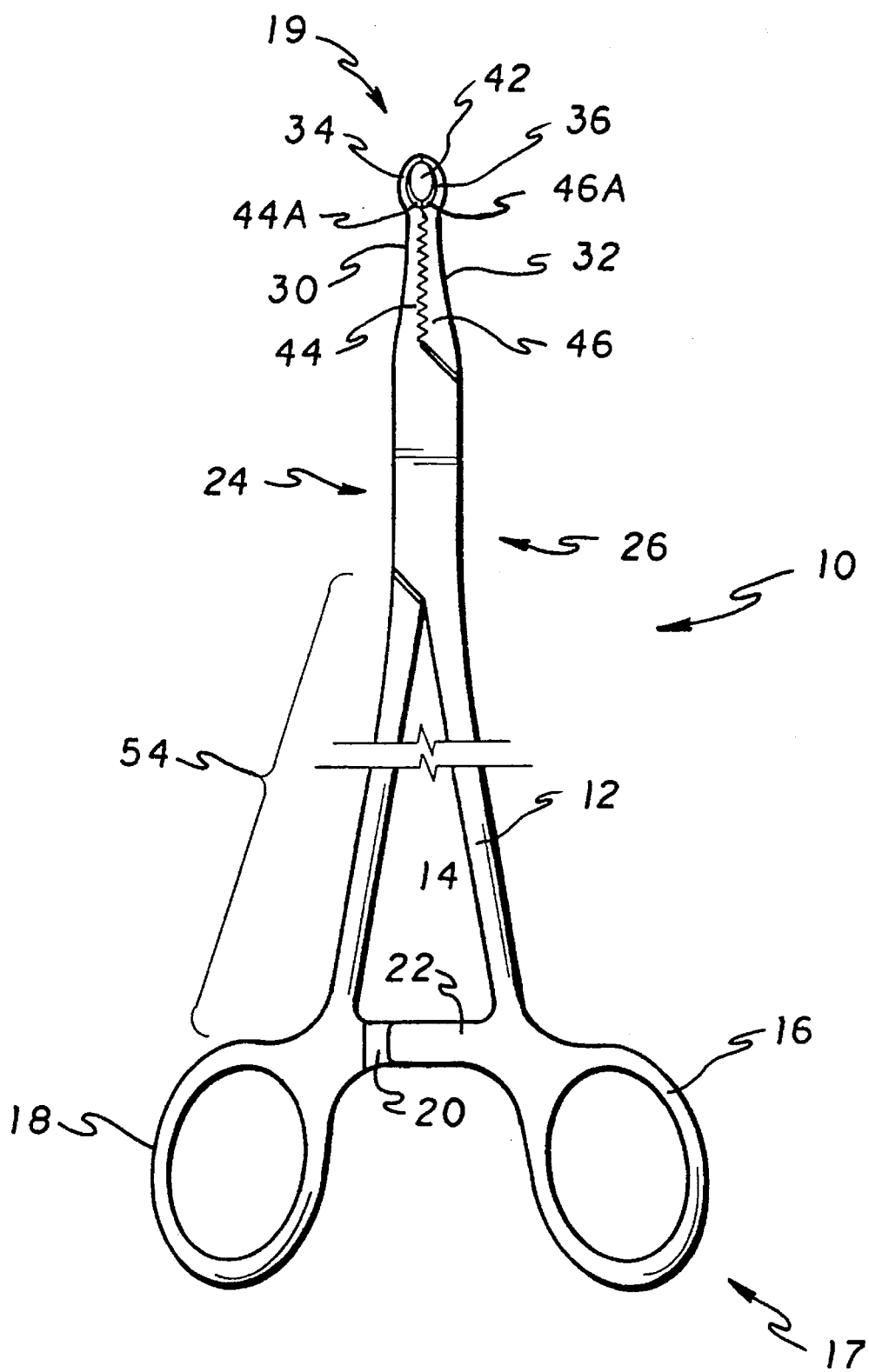
FIG. 2 is a plan view of the forceps of the present invention, in a closed position, higlighting the small, oval-shaped opening at the extreme distal end of the grasping tip and the mating serration behind the opening.

The apparatus of the present invention comprises a simple and highly effective device for grasping, elevating, and rotating tubular tissue, especially the vas deferens or vagus nerve. The overall apparatus 10 includes arms 12, 14, each having handle sections 16, 18 at a first end 17. The handle sections 16, 18 have sawtooth extensions 20, 22 projecting inward from the handle sections 16, 18. The sawtooth extensions 20, 22 engage one another when the forceps 10 is in a closed position, as shown in FIG. 2.

Figure 1:
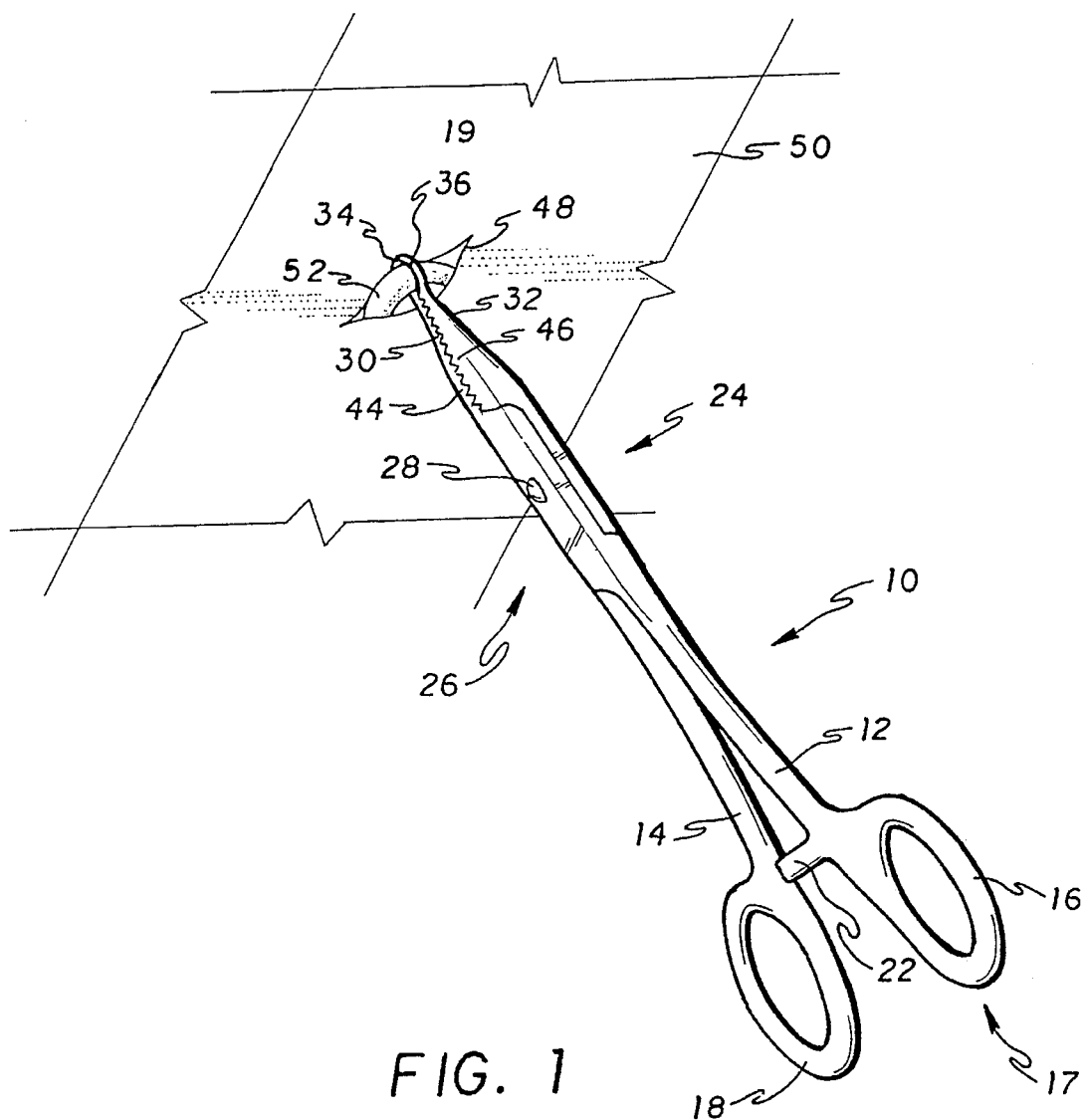
FIG. 1 is an enviromental, perspective view of the invention showing the forceps effective elevation and rotation of a vas deferens out from a minute incision, without destruction or tearing or adjacent tissue.

The arms 12, 14 also have pivoting sections 24, 26 next to the handle sections 16, 18. Along these pivoting sections 24, 26, the arms 12, 14 cross one another and are connected at their crossing by a cross-over stud 28, as shown in FIG. 1. The preferred length between stud 28 and first end 17 is approximately 10.5 centimeters.

The arms 12, 14 additionally have grasping sections 30, 32 at a second end 19. The length from stud 28 to second end 19 is approximately 3 centimeters. The grasping sections 30, 32 comprise grasping tips 34, 36 which define and semi-enclose open, grasping regions 38, 40. As may be seen, from FIG. 3 particularly, the juxtaposition of such grasping regions 38, 40 upon placement of the forceps 10 in a closed orientation, forms an oval opening 42, somewhat elongated along an axis parallel to a long axis of the forceps. Sample dimensions for the opening are 0.25 centimeters in width and 0.40 centimeters in length. The grasping sections 30, 32 also have mating serrations 44, 46, which lie farther from the second end than the grasping tips 34, 36 and grasping regions 38, 40, and immediately adjacent to said tips 34, 36 and said regions 38, 40. These serrations 44, 46 faciliate the grasping function of the forceps 10 by providing additional frictive structure. The grasping tips 34, 36 have a v-shape formed by inverted v-shaped beveled surfaces or crests 44a, 46a, extending away from arms 12, 14 into oval opening 42. The v-shaped surfaces 44a, 46a are disposed circumferentially around inner edges or facing surfaces of the grasping tips 34, 36. The v-shaped surfaces 44a, 46a may extend along the entire facing surfaces of grasping tips 34, 36 or may extend only partially along the facing surfaces, preferably along the lower half of the facing surfaces closer to the first end 17. The v-shaped surfaces 44a, 46a project at a greater height at an end of the grasping tips 34, 36 farther from the second end 19 than at an end of the grasping tips 34, 36 nearer to the second end 19. The v-shaped surfaces 44a, 46a culminate in crest tips. The crest tips may be sharp or may be rounded, preferably with a radius of curvature of about 500 micrometers. The v-shaped surfaces 44a, 46a further faciliate the grasping function of the forceps 10 by providing additional frictive structure.

Figure 3:
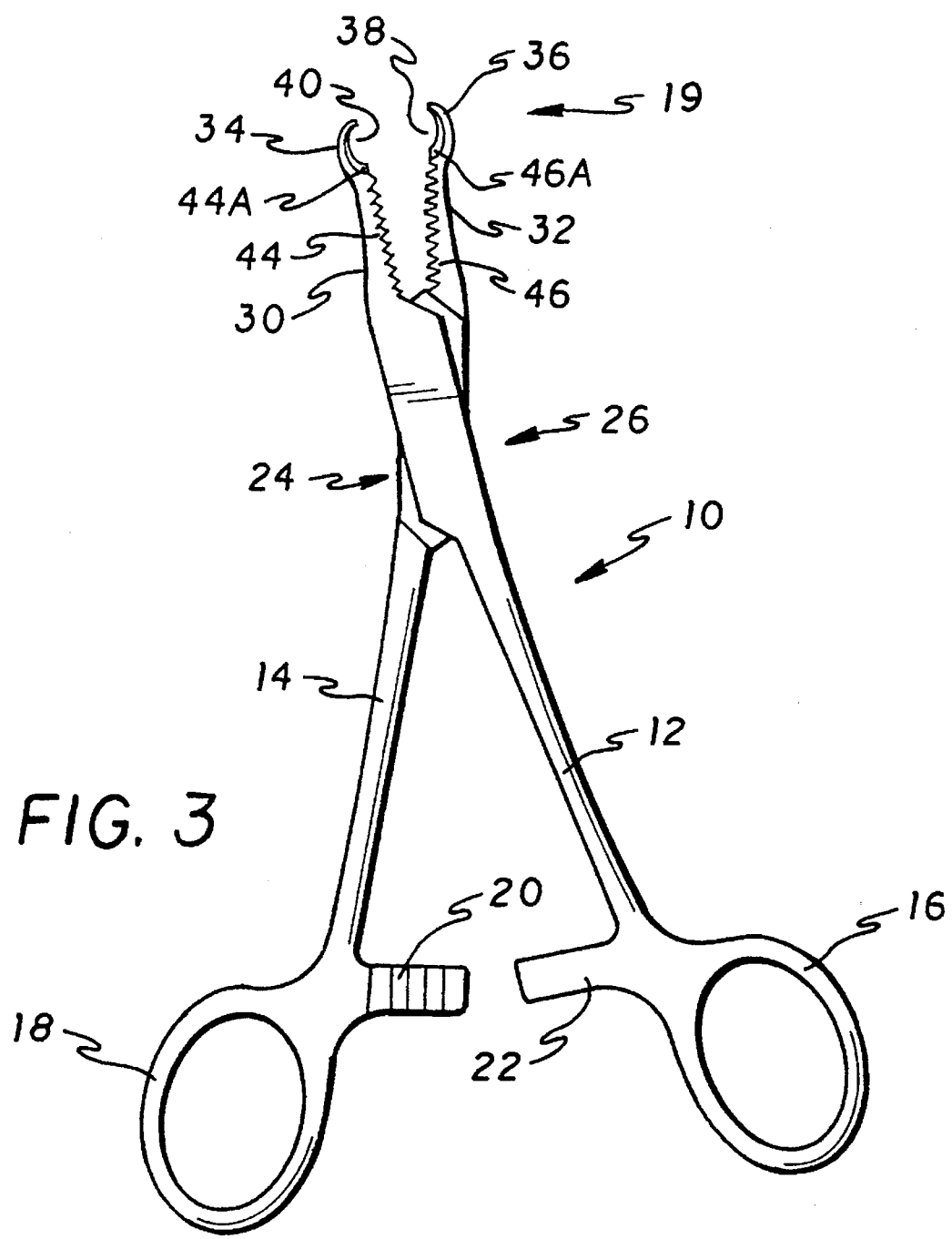
FIG. 3 is a plan view of the forceps of the present invention, in a pre-grasping or open position.
Figure 4:
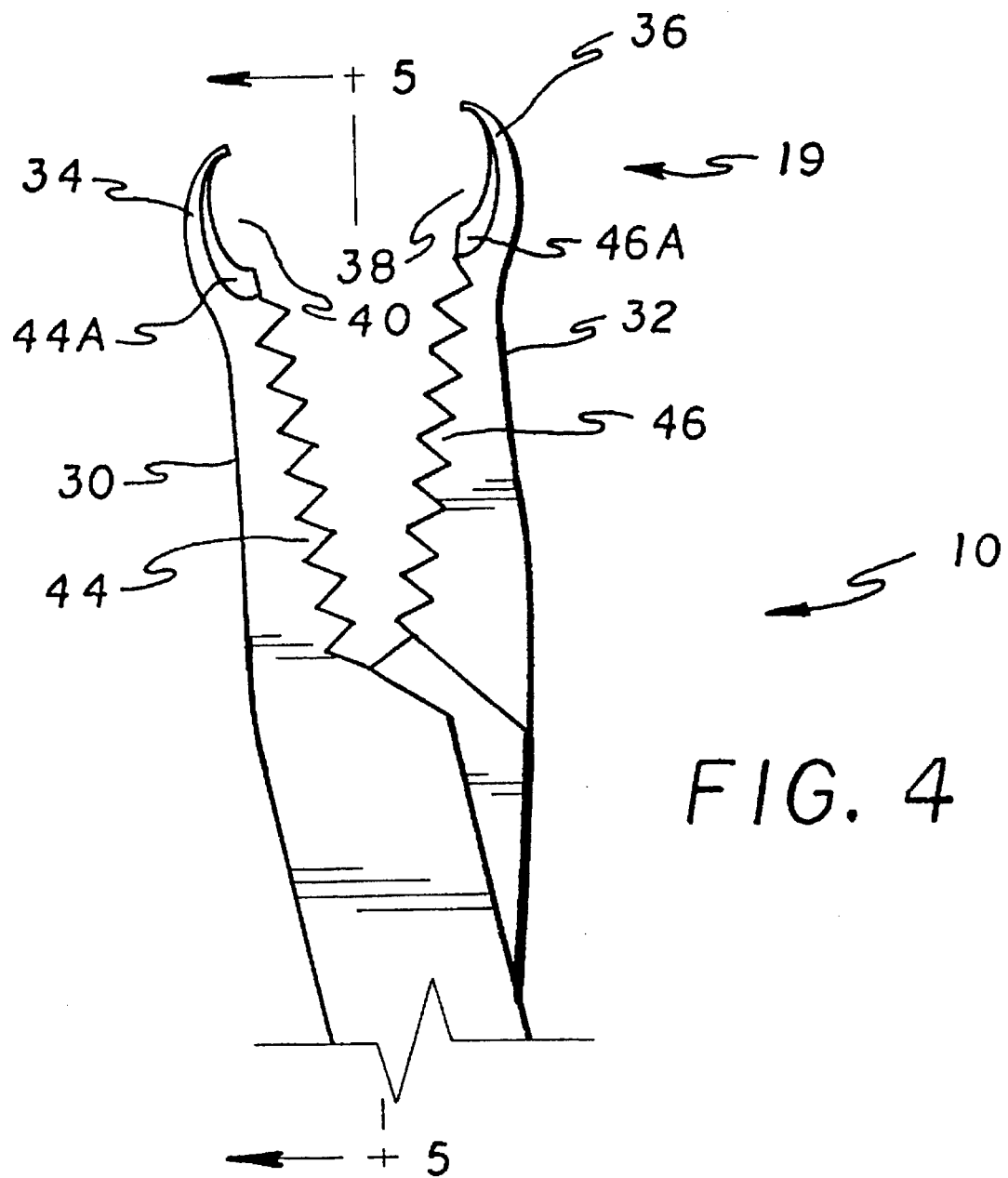
FIG. 4 is a close-up view of the grasping tips of the invention, depicting the thin, pincer-like grasping tips and the beveled bottom portion of the clamping loop.
Figure 5:
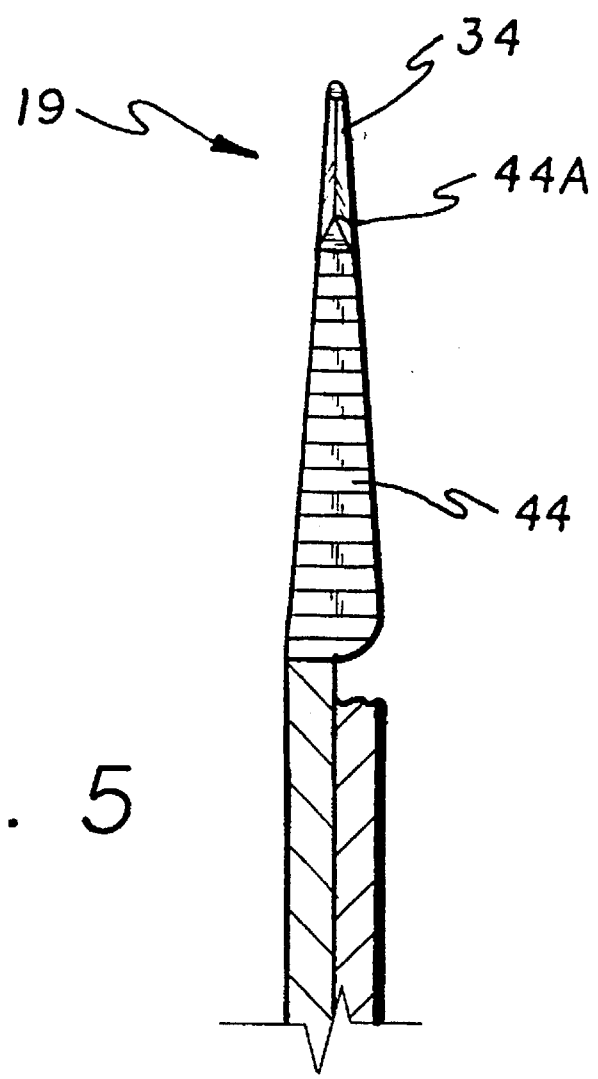
FIG. 5 is a cross-section view of the grasping end of the invention, depicting the tiny width of that end.

In use of the forceps during a vasectomy procedure, a user first creates an incision 48 in the scrotum 50. Because of the compact and efficient shape of the present forceps 10, such an incision 48 can be smaller than an incision (not shown) provided using forceps of the prior art (not shown). More specifically, the grasping tips 34, 36 are extraordinarily narrow, as viewed from any perspective, FIGS. 1 and 5. Additionally, the grasping regions 38, 40 are positioned at a most extreme portion of the second end 19, so that there is essentially no distance between the grasping regions 38, 40 and the most extreme portion of the second end 19, as shown in FIG. 3. As will be appreciated, limitations on the character of submitted drawings make it necessary to depict even very thin objects with with some distance between edges; however, it must be understood that the locations of the grasping regions 38, 40 are as close to the most extreme portion of the second end 19 as is physically and practically possible. This positioning of the grasping regions 38, 40 comprises a crux of the innovation of this invention, insofar as this positioning enables the user to grasp tubular tissue such as the vas deferens 52 without contacting or grasping tissue beyond the location of the tubular tissue sought to be grasped, and without making a large incision.

With more particularity, the dimensions of the generally oval shaped opening 42 are about 0.40 centimeters in length and 0.25 centimeters in width, and the distance between the most extreme portion of the second end 19 of arms 12, 14, and the end of the opening nearest said tip is less than 1 millimeter. These dimensions are depicted approximately in FIGS. 2 and 3, within the constraints of limitations on submitted drawings. It may be seen particularly from FIG. 3, that the small overall grasping sections' 30, 32 size, the closed loop 42, and the proximity of this loop 42 to the distal extremity of the forcep arms 12, 14 that enables the use and advantages of the present forceps 10. Moreover, the small size and extreme location of the grasping sections 30, 32 and the closed loop 42, as well as the proximity of this end loop to the distal extremity of the forcep arms 12, 14, enable the user to efficiently tip up or rotate the vas deferens 52 to be out of the incision 48 during a vasectomy so that its covering sheath (not shown) can be dissected. The overall procedure, as previously described herein, is thereby enabled with a greatly shortened time for the surgery, and with more precision in lifting, rotating and initially locating the vas deferens. In other words, the shape and size of the grasping sections 30, 32 permit the user to firmly grasp the vas deferens 52, to lift it up and out of the incision 48, and to rotate it all in one motion, thus exposing the surrounding sheath for dissection. Once the duct 52 is exposed, it can be easily cut and ligated. Significantly, the risk of slippage of the vas deferens 52, when it is rotated during the vasectomy procedure, is greatly reduced. The mating serrations, forming a line matching the lengthwise extension of the instrument, closes firmly behind the opening 10a, 12a.

A method of use of the apparatus 10 would include the steps of: Lowering grasping sections 22 of arms 12, 14 of a forceps instrument 10 according to the invention into the incision 48; causing grasping regions 38, 40 located at an extreme end of the forceps 10 to surround and encompass the vas deferens 52; closing the instrument 10, with serrations 44, 46 in mating position and engaging sawtooth projections together so the device 10 is locked closed, as shown in FIG. 2; lifting the vas deferens 52 out of the incision 48; and rotating it to facilitate dissection of the surrounding sheath (not depicted). Subsequently, the vas deferens is severed and resulting cut ends (not shown) are ligated closed. Alternately, the ligations (not shown) may be placed first, and the vas deferens 52 cut between the ligations. The forceps 10 is released, and standard surgical procedures follow.

A second embodiment of the invention comprises a forceps 10 useful for interventions in the lower esophagus and stomach. The foregoing description of the operation of the forceps 10 of the present forceps is likewise applicable to a surgical procedure commonly performed in connection with the lifting of the vagus nerve in the lower esophagus or in the stomach. Referring to FIG. 2, such an operation is performed most efficiently by adding approximately six centimeters to the length 54 of the arms 12, 14 of the forceps 10. Thereby increasing the length from the pivot point 28 to the first end 17 to approximately 16.5 centimeters in order to accommodate the depth of the insertion, when the lower esophagus or stomach is the target area for the surgery.

It is to be understood that the present invention is not limited to the embodiments described above, but encompasses any and all embodiments within the scope of the following claims.

I claim:

1. A forceps comprising:
   a pair of elongated forceps arms, each elongated arm having an aperture therethrough, a first end at least 10.5 centimeters from the aperture, and a second end approximately 3 centimeters from the aperture;
   a stud disposed wholly within the apertures of each elongated arm, said stud pivotally connecting said pair of elongated arms;
   a handle formed at the first end of each elongated arm; and
   a grasping section formed at the second end of each elongated arm, each said grasping section terminating in a v-shaped grasping tip, each said tip together defining an oval opening when said forceps are closed, said opening being not more than 0.40 centimeters in diameter in a direction parallel with said elongated arms and not more than 0.25 centimeters in diameter in a direction perpendicular to said elongated arms, said opening disposed within one millimeter of the second end of said elongated arms, and said grasping section also including a serrated portion adjacent to said grasping tip.

2. The forceps according to claim 1 wherein:
   said first end is not more than 11 centimeters from said aperture.

3. The forceps according to claim 1 wherein:
   said first end is approximately 16.5 centimeters from said aperture.

4. The forceps according to claim 1, wherein:
   said v-shaped grasping tips terminate in a sharp edge.

5. The forceps according to claim 1, wherein:
   said v-shaped grasping tips terminate in a rounded edge having a radius of curvature of about 500 micrometers.

* * * * *